(12) United States Patent
Rondeau

(10) Patent No.: US 9,101,482 B2
(45) Date of Patent: Aug. 11, 2015

(54) ONE-PASS OSTOMY DRAINING DEVICE

(75) Inventor: Phillipe Joseph Andre Rondeau, Carbonear (CA)

(73) Assignee: UNCLE PHIL'S THINK TANK INC., Mount Pearl, Newfoundland (CA)

(*) Notice: Subject to any disclaimer, the term of this patent is extended or adjusted under 35 U.S.C. 154(b) by 0 days.

(21) Appl. No.: 13/813,362

(22) PCT Filed: Jul. 30, 2010

(86) PCT No.: PCT/CA2010/001207
§ 371 (c)(1),
(2), (4) Date: Apr. 3, 2013

(87) PCT Pub. No.: WO2012/012864
PCT Pub. Date: Feb. 2, 2012

(65) Prior Publication Data
US 2013/0181006 A1  Jul. 18, 2013

(51) Int. Cl.
*B65D 35/28* (2006.01)
*A61F 5/44* (2006.01)
*A61F 5/445* (2006.01)

(52) U.S. Cl.
CPC ............... *A61F 5/4404* (2013.01); *A61F 5/445* (2013.01)

(58) Field of Classification Search
CPC .... A61M 27/00; B65B 69/0016; A61F 5/445; A61F 5/4404
USPC .................. 222/95, 102, 103, 1; 128/DIG. 24, 128/103.1; 606/209; 417/477.1
See application file for complete search history.

(56) References Cited

U.S. PATENT DOCUMENTS

| | | | | |
|---|---|---|---|---|
| 1,311,085 A * | 7/1919 | Mucher | ........................ | 222/102 |
| 1,386,966 A * | 8/1921 | Slade | ............................. | 222/102 |
| 1,777,906 A * | 10/1930 | Winsor | ............................ | 222/93 |
| 2,903,162 A * | 9/1959 | Regan | ............................. | 222/99 |
| 3,142,074 A * | 7/1964 | Reich | ............................. | 7/135 |
| 3,606,090 A * | 9/1971 | Byers | ............................. | 222/102 |
| 4,164,223 A * | 8/1979 | Munib | ............................ | 606/209 |
| 4,639,251 A * | 1/1987 | Kirkland | ...................... | 604/260 |
| 4,642,106 A | 2/1987 | Downey | | |
| 5,277,335 A * | 1/1994 | Okami et al. | ................ | 222/102 |
| 5,297,699 A | 3/1994 | Barchus | | |
| 5,490,613 A * | 2/1996 | Taylor et al. | ................. | 222/102 |
| 5,657,903 A * | 8/1997 | Roberts | ........................ | 222/102 |
| 6,155,458 A | 12/2000 | Picard | | |
| 2002/0011497 A1 * | 1/2002 | Farris | ............................ | 222/102 |

FOREIGN PATENT DOCUMENTS

EP  0 210 142  1/1987

OTHER PUBLICATIONS

International Search Report of PCT/CA2010/001207, Apr. 5, 2011.

* cited by examiner

*Primary Examiner* — Kevin P Shaver
*Assistant Examiner* — Robert Nichols, II
(74) *Attorney, Agent, or Firm* — Collard & Roe, P.C

(57) ABSTRACT

A device for emptying an ostomy bag includes a pair of elongate members, each having bag engagement members and first and second ends. The elongate members are adapted to extend substantially across a width of the ostomy bag. A hinge member is in cooperative engagement with the second ends of the elongate members and gripping members are provided at the first ends of the elongate members. The pair of elongate members are moveable from an open position where the elongate members extend outwardly from the hinge member away from each other and a closed position wherein the elongate members are generally parallel to each other.

2 Claims, 3 Drawing Sheets

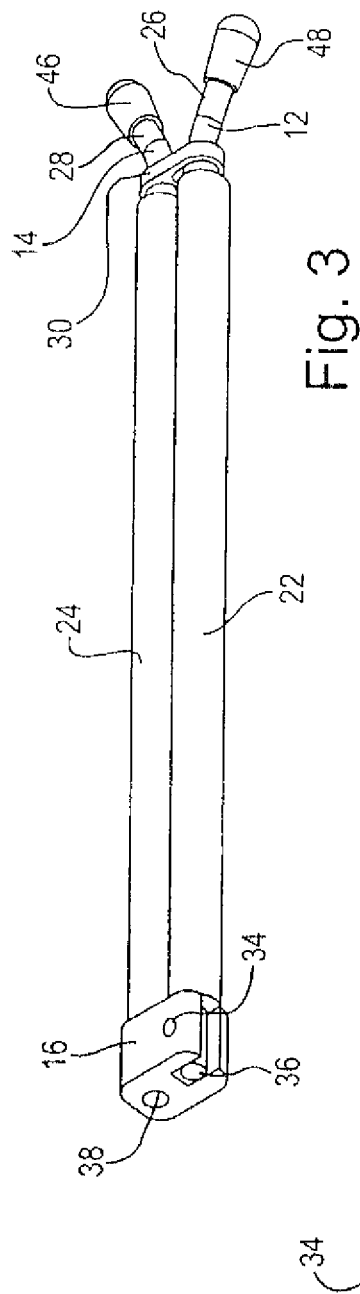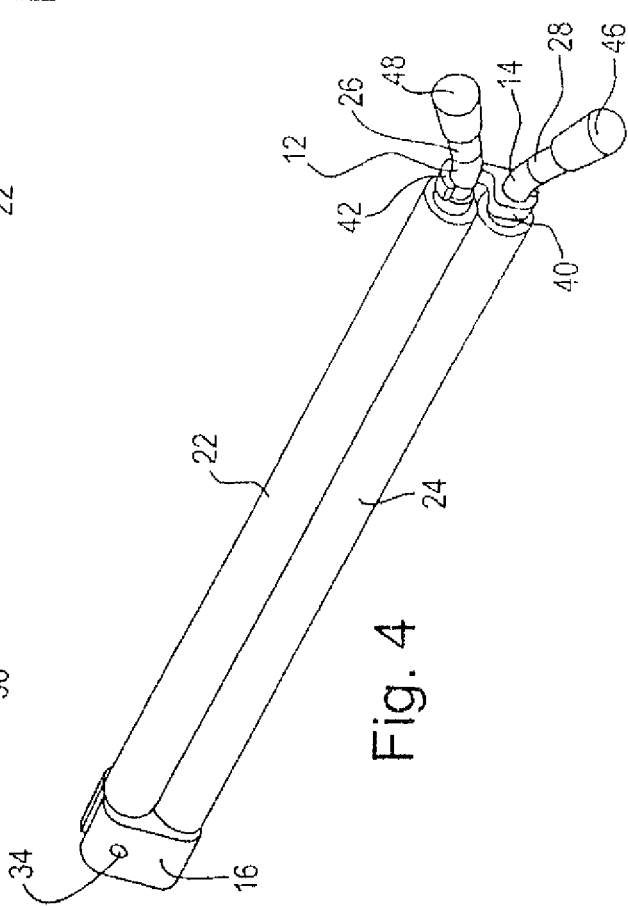

ONE-PASS OSTOMY DRAINING DEVICE

CROSS REFERENCE TO RELATED APPLICATIONS

This application is the National Stage of PCT/CA2010/001207 filed on Jul. 30, 2010, the disclosure of which is incorporated by reference. The international application under PCT article 21(2) was published in English.

BACKGROUND OF THE INVENTION

1. Field of the Invention

The present invention relates to a device to aid in the emptying or evacuation of reusable bags or pouches. More particularly, the present invention relates to a device for assisting with emptying reusable drainage bags or pouches, such as ostomy bags.

2. Background

Ostomy bags or pouching systems have been used for many years by a great many people for the evacuation and collection of body wastes, where such individuals have undergone surgery, such as colostomy or ileostomy surgeries, to divert the waste material through a surgically created path or stoma.

Ostomy bags or systems usually consist of a mounting member, commonly called a wafer or baseplate, and a collection pouch or bag. The ostomy bag can be disposable or reusable. In the case of reusable ostomy bags, the bags must be emptied or drained and cleaned prior to reuse.

Currently, to empty an ostomy bag, it is necessary to hold the bag over the toilet or other suitable receptacle, open the drainage opening and manipulate the bag, such as by squeezing manually, to aid in the complete emptying of the bag. The emptying procedure can be time consuming, disagreeable and messy.

U.S. Pat. No. 4,642,106 discloses an implement or tool for facilitating the drainage of an ostomy bag. The tool is a single unitary piece of molded plastic having a handle portion comprised of two sections joined at a hinge. Elongated engagement members extend from each of the handle members which are adapted to engage the walls of an ostomy bag therebetween. When emptying an ostomy bag, the bag is placed between the elongated members with the elongated members in engagement with the bag and the device is moved along the bag forcing the contents towards the drainage opening. The elongated members do not extend the entire width of the bag and thus it is necessary to repeat the procedure for each side of the ostomy bag. As the elongated members are in engagement with the walls of the bag, sufficient force must be applied to the device to slide the device over the walls of the ostomy bag and push the contents towards the drainage opening of the bag.

SUMMARY OF THE INVENTION

In accordance with one embodiment of the present invention, there is provided a device for assisting in emptying of an ostomy bag. The device includes a pair of elongate members, each having bag engagement members and first and second ends. The elongate members are adapted to extend substantially across a width of the ostomy bag to be emptied. A hinge member is provided in cooperative engagement with the second ends of the elongate members. Gripping members are provided at the first ends of the elongate members. The pair of elongate members are moveable from an open position where the elongate members extend outwardly from the hinge member away from each other and a closed position wherein the elongate members are generally parallel to each other.

Another embodiment of the present invention provides a device for emptying an ostomy bag comprising: a pair of elongate members each having bag engagement members and first and second ends; a hinge member at the second ends of said elongate members; and a releasable locking means in cooperative engagement with the first ends of the elongate members. At least one of said pair of elongate members is pivotally secured to the hinge member so that it is movable from a first position parallel to the other of said pair of elongate members and a second position at an angle to said other of said pair of elongate members.

In accordance with a still further embodiment of the present invention there is provided a method for emptying the contents of an ostomy bag through a drainage opening of the ostomy bag. An ostomy bag emptying device is provided having a pair of elongate members which extend substantially across the width of the ostomy bag to be emptied, where the elongate members have bag engagement members. A hinge member is in cooperative engagement with one end of each of the elongate members and gripping means are provided at the other end of each of said elongate members. In the method, the elongate members are opened by extending one of the elongate members in a direction away from the other of the elongate members. One of the elongate members is placed on a front surface of the ostomy bag to be emptied and the other of the elongate members is placed on a back surface of the ostomy bag near the top of the ostomy bag at a distance from the drainage opening. The ostomy bag is held in position over a suitable receptacle, such as a toilet or other such receptacle and the drainage opening of the ostomy bag is opened. The elongate members are moved towards each other, to a closed position so that the elongate members are in a generally parallel orientation with the bag engagement members engaging the bag. The elongate members are maintained in the closed position and moved down the length of the bag towards the drainage opening to move the contents towards and through the drainage opening. The elongate members are then moved to the open position to remove the same from engagement with the ostomy bag.

Preferably the elongate members of the device are of a length such that they extend substantially across the entire width of the ostomy bag. In particularly preferred embodiments, the elongate members are rods which are of a length which is greater than the width of the ostomy bag.

The device of the present invention permits the ready evacuation of the contents of an ostomy bag in a simple, clean and effective manner; the device only requiring a single pass over the ostomy bag to fully evacuate the contents. Further, the device has the advantage that it is portable and can be easily and readily carried by an individual user.

BRIEF DESCRIPTION OF THE DRAWINGS

FIG. 3 is a perspective view of the first embodiment of the present invention in a closed position;

FIG. 4 is a further perspective view of the first embodiment of the present invention in a closed position.

DETAILED DESCRIPTION

Figure 1:
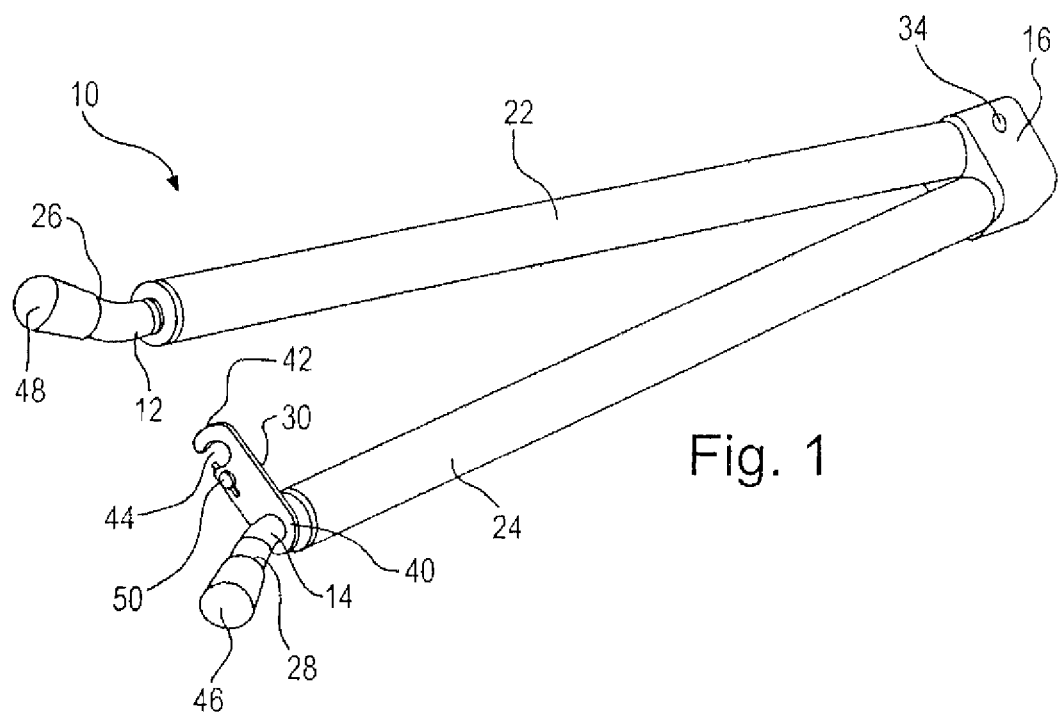
FIG. 1 is a perspective view of one embodiment of the present invention in an open position.

Referring now to the drawings, FIGS. 1 to 4 illustrate one embodiment of the ostomy drainage device 10 of the present invention. The drainage device 10 includes a pair of elongated members 12, 14 connected at one end through a hinge member 16. The elongate members 12, 14 are each connected to the hinge member 16 through connecting rods 36, 38 which project outwardly from the end thereof. The elongate members 12, 14 are in the form of elongate rods. Rollers 22, 24 are mounted on the elongate rods. The ends of the elongate members 12, 14, opposite the hinge 16 include gripping ends 26, 28 and a releasable lock mechanism 30.

The gripping ends 26, 28 are formed by a bend in the elongate rods 12, 14 such that the gripping ends 26, 28 extend outwardly away from each other.

Figure 2:
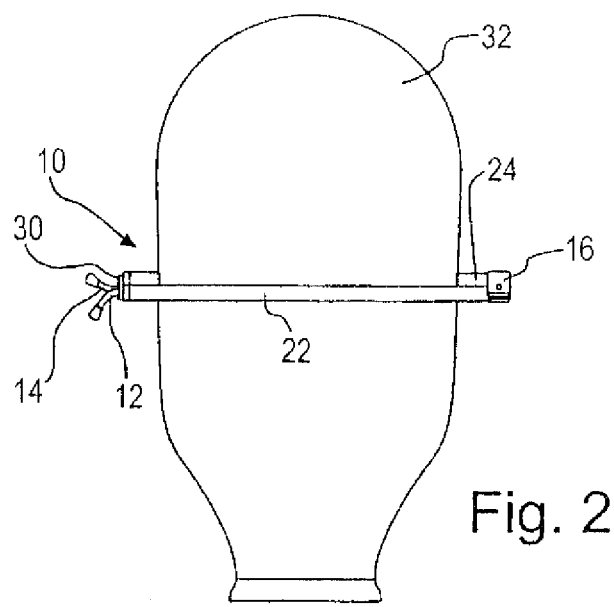
FIG. 2 is a front elevational view of the device of the present invention in use on an ostomy bag.

As shown in FIG. 2, elongate members 12, 14 are of a dimension to fit across the full width of an ostomy bag 32, permitting the bag 32 to be emptied in a very simple and quick manner with one pass of the device 10 over the bag 32.

In use, a user opens the device 10, by disengaging the lock mechanism 30 moving the elongate member 12 away from the other elongate member 14. One of the rollers 22 is positioned on the front face of the bag 32 and the second roller 24 is placed on the back face of the bag 32 and the lock mechanism 30 engaged so that the rollers 22, 24 are locked into position parallel to each other and engaging the ostomy bag 32. The ostomy bag 32 is then placed over a toilet or other suitable receptacle and the drainage port opened. The device 10 is then moved down the ostomy bag 32 thereby pushing the contents of the ostomy bag 32 towards and through the drainage opening into the toilet or other suitable receptacle.

Preferably, the hinge member 16 fixedly retains the rod 38 of the elongate member 14 with the rod 36 of the other elongate member 12 being secured for pivoting rotation with respect to the hinge member 16. The hinge member 16 preferably restricts movement of the rotatable elongate member 12 to a maximum angle of 15 degrees.

The elongate member 12 which is rotatable is pivotally secured to the hinge member 16 through a pivot pin 34.

Preferably the locking mechanism 30 is in the form of a latch member having one end 40 fixedly secured to the gripping end 28 of one elongate member 14 and the other end 42 of the latch member having an opening 44 to fit onto the gripping end 26 of the other elongate member 12. A releasable lock means 50 is provided to releasably retain the locking mechanism 30 in position secured on the elongate member 12.

Preferably the gripping ends 26, 28 of the elongate members 12, 14 have rubber end caps 46, 48.

Preferably, the elongate members 12, 14 are made of metal rods approximately 5 to 9 inches long, most preferably between about 7 and 8 inches long. The rod preferably has a diameter of 3/16 of an inch.

The rollers are preferably of a plastic material and can be approximately 4-8 inches in length and preferably have a diameter of 3/8 inch.

Figure 5:
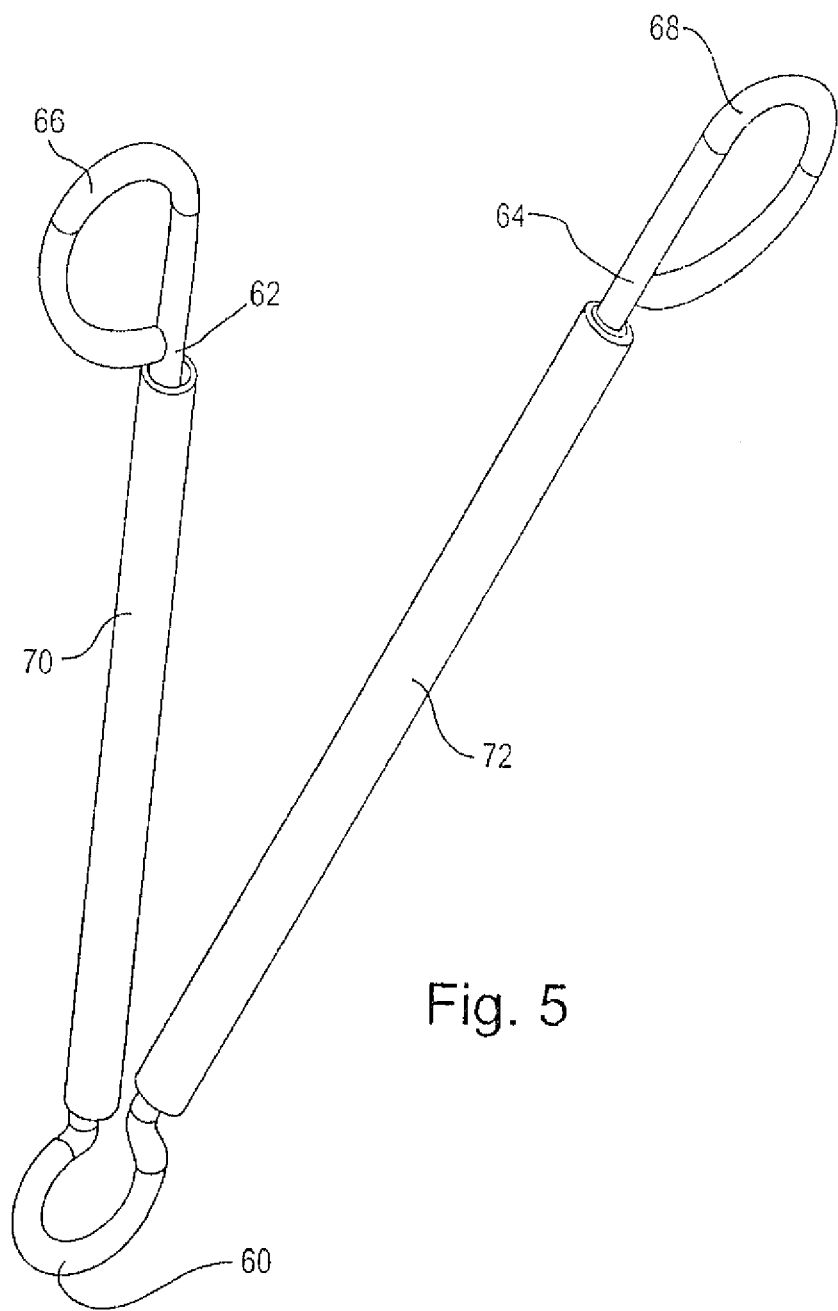
FIG. 5 is perspective view of a second embodiment of the present invention.

FIG. 5 shows a second embodiment of the present invention where the device is comprised of a unitary elongated rod like member which is bent in a circular bend to form a hinge 60 and a pair of elongated arms 62, 64 extending from the hinge 60. The elongated arms 62, 64 each include a gripping member 66, 68 at the free end. The gripping members 66, 68 are in the form of a loop-like members. Roller members 70, 72 are provided on the elongated arms 62, 64. In use, the gripping members 66, 68 are grasped by a user and the arms 62, 64 are pressed together in a generally parallel arrangement, one on each side of the ostomy bag. The device is moved down the ostomy bag to move the contents therein towards and out the drainage opening.

While the invention has been described in detail with reference to preferred embodiments thereof, it will be understood by those skilled in the art that various modifications and changes can be made thereto without departing from the spirit and scope of the invention.

What is claimed is:

1. A method for emptying the contents of an ostomy bag through a drainage opening of the ostomy bag, comprising the steps of:

providing an ostomy bag emptying device having a pair of elongate members which extend substantially across the width of the ostomy bag to be emptied, said elongate members having bag engagement members in the form of rollers, a hinge member in cooperative engagement with one end of each of the elongate members and gripping means at the other end of each of said elongate members;

opening the elongate members by extending each of the elongate members in a direction away from the other of said elongate members;

placing one of the elongate members on a front surface of the ostomy bag and the other of the elongate members on a back surface of the ostomy bag near the top of the ostomy bag at a distance from the drainage opening;

holding the ostomy bag over a receptacle;

opening the drainage opening of the ostomy bag;

moving the elongate members towards each other, to a closed position so that the elongate members are in a generally parallel orientation with the bag engagement members engaging the bag;

maintaining the elongate members in the closed position;

rolling the elongate members down the length of the bag towards the drainage opening to move the contents towards and through the drainage opening; and opening the elongate members to remove from the ostomy bag; wherein the elongate members move the contents of the bag towards the drainage opening in a single pass over the bag.

2. The method of claim 1, wherein the step of maintaining the elongate members in the closed position comprises locking the elongate members in a closed position with a lock member.

* * * * *